US 7,771,388 B2

(12) United States Patent
Olsen et al.

(10) Patent No.: US 7,771,388 B2
(45) Date of Patent: Aug. 10, 2010

(54) STEERABLE CATHETER SYSTEM

(76) Inventors: Daniel Olsen, 70 E. Shawnee Trail, Wharton, NJ (US) 07885; Randy David B. Grishaber, 25 Village square Dr., Asbury, NJ (US) 08802; Chao-Chin Chen, 5 Jason St., Edison, NJ (US) 08820; Rudy Cedro, 8 Old Jericho Rd., Clinton, NJ (US) 08809; Jin Park, 300 Parsippany Rd., Parsippany, NJ (US) 07054

( * ) Notice: Subject to any disclaimer, the term of this patent is extended or adjusted under 35 U.S.C. 154(b) by 381 days.

(21) Appl. No.: 11/548,990

(22) Filed: Oct. 12, 2006

(65) Prior Publication Data

US 2007/0191765 A1    Aug. 16, 2007

Related U.S. Application Data

(60) Provisional application No. 60/725,679, filed on Oct. 12, 2005.

(51) Int. Cl.
*A61M 31/00* (2006.01)
*A61M 37/00* (2006.01)

(52) U.S. Cl. .................................. 604/95.04

(58) Field of Classification Search ............. 604/95.04, 604/95.03, 528, 523–524
See application file for complete search history.

(56) References Cited

U.S. PATENT DOCUMENTS

| | | |
|---|---|---|
| 4,719,924 A | 1/1988 | Crittenden |
| 4,757,827 A | 7/1988 | Buchbinder |
| 4,813,434 A | 3/1989 | Buchbinder |
| 4,815,478 A | 3/1989 | Buchbinder |
| 4,886,067 A | 12/1989 | Palermo |
| 4,921,482 A | 5/1990 | Hammerslag |
| 4,940,062 A | 7/1990 | Hampton |
| 4,998,916 A | 3/1991 | Hammerslag |
| 5,037,391 A | 8/1991 | Hammerslag |
| 5,060,660 A | 10/1991 | Gambale |
| 5,159,937 A | 11/1992 | Tremulis |
| 5,190,050 A | 3/1993 | Nitzsche |
| 5,203,772 A | 4/1993 | Hammerslag |
| 5,372,587 A | 12/1994 | Hammerslag |
| 5,480,382 A | 1/1996 | Hammerslag |

(Continued)

FOREIGN PATENT DOCUMENTS

EP    1174077 A1    1/2002

(Continued)

OTHER PUBLICATIONS

International Search Report re: PCT/US2006/039850 dated Sep. 4, 2007.

*Primary Examiner*—Nicholas D Lucchesi
*Assistant Examiner*—Rebecca E Eisenberg

(57) ABSTRACT

This invention relates to devices for navigating passageways in a body, and in particular, to a steerable catheter that can be used to navigate the tortuous anatomy of a body's vasculature. In one embodiment of the invention the deflectable catheter comprises an inner catheter body having a first strut spine member and a cantilevered second strut tang member. An outer catheter body is cooperatively associated with the second strut tang member and an actuator is cooperatively associated with the first strut spine member. The actuator is slideably engaged within the outer catheter body.

25 Claims, 9 Drawing Sheets

U.S. PATENT DOCUMENTS

| | | |
|---|---|---|
| 5,531,686 A | 7/1996 | Lundquist et al. |
| 5,882,333 A | 3/1999 | Schaer |
| 6,059,739 A | 5/2000 | Baumann |
| 6,126,649 A | 10/2000 | VanTassel |
| 6,146,338 A | 11/2000 | Gardeski |
| 6,702,780 B1 * | 3/2004 | Gilboa et al. ............ 604/95.04 |
| 7,128,718 B2 | 10/2006 | Hojeibane |
| 7,481,778 B2 | 1/2009 | Cedro |
| 7,520,863 B2 | 4/2009 | Grewe |
| 2002/0165534 A1 | 11/2002 | Hayzelden |
| 2003/0045831 A1 | 3/2003 | Ponzi et al. |
| 2004/0097819 A1 * | 5/2004 | Duarte ....................... 600/509 |

FOREIGN PATENT DOCUMENTS

| | | |
|---|---|---|
| WO | WO 94/14494 A2 | 7/1994 |
| WO | WO 97/31677 A1 | 9/1997 |
| WO | WO 01/68178 A1 | 9/2001 |
| WO | WO 2007008565 A1 * | 1/2007 |

* cited by examiner

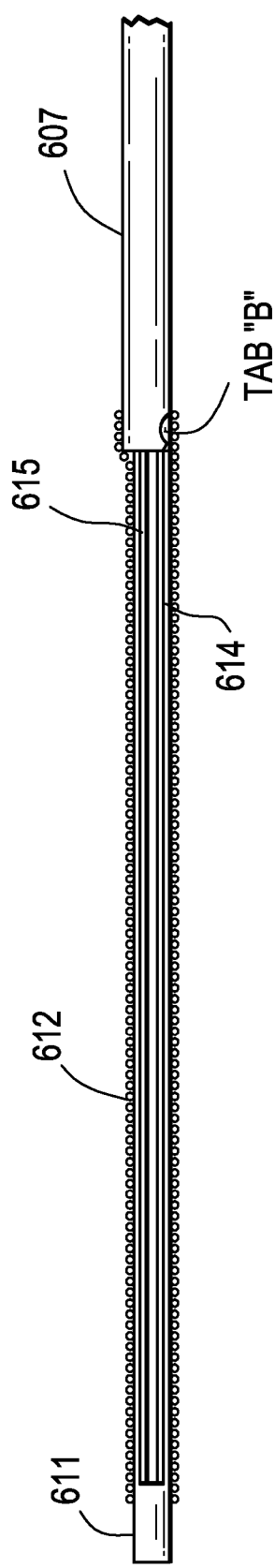
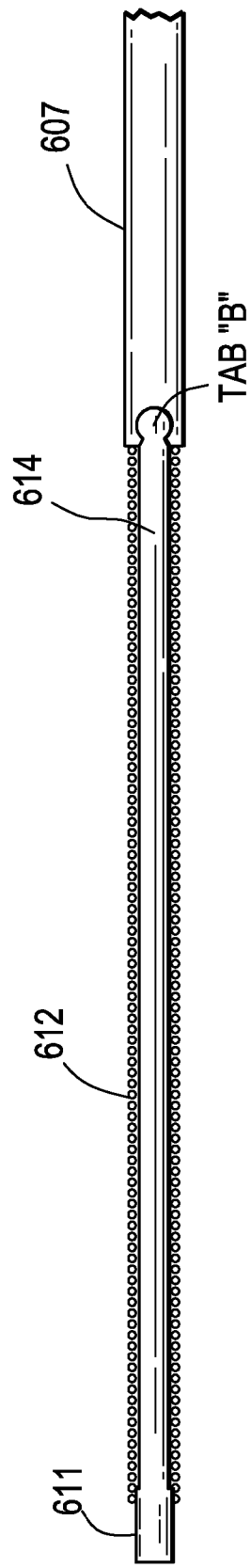

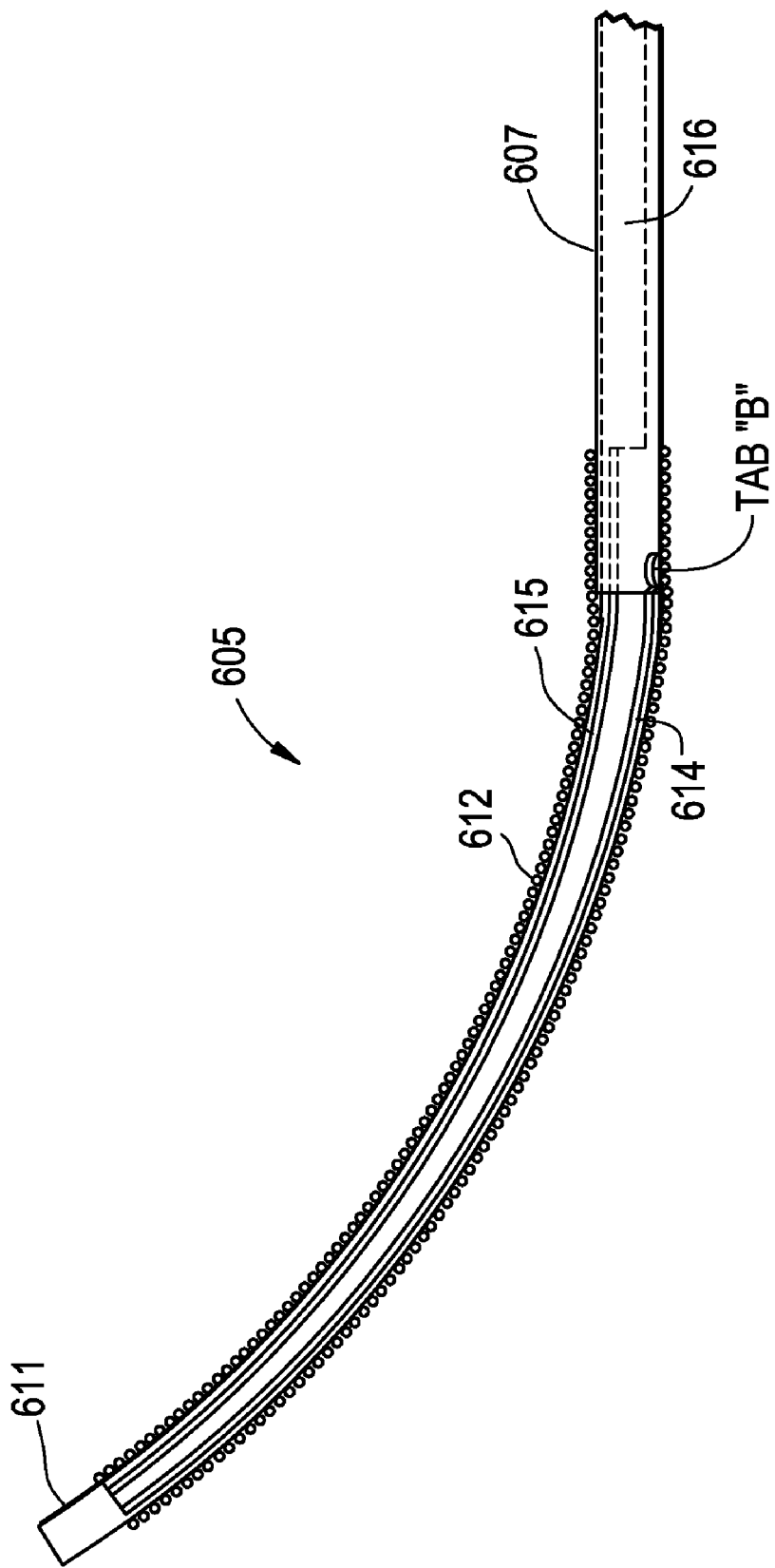

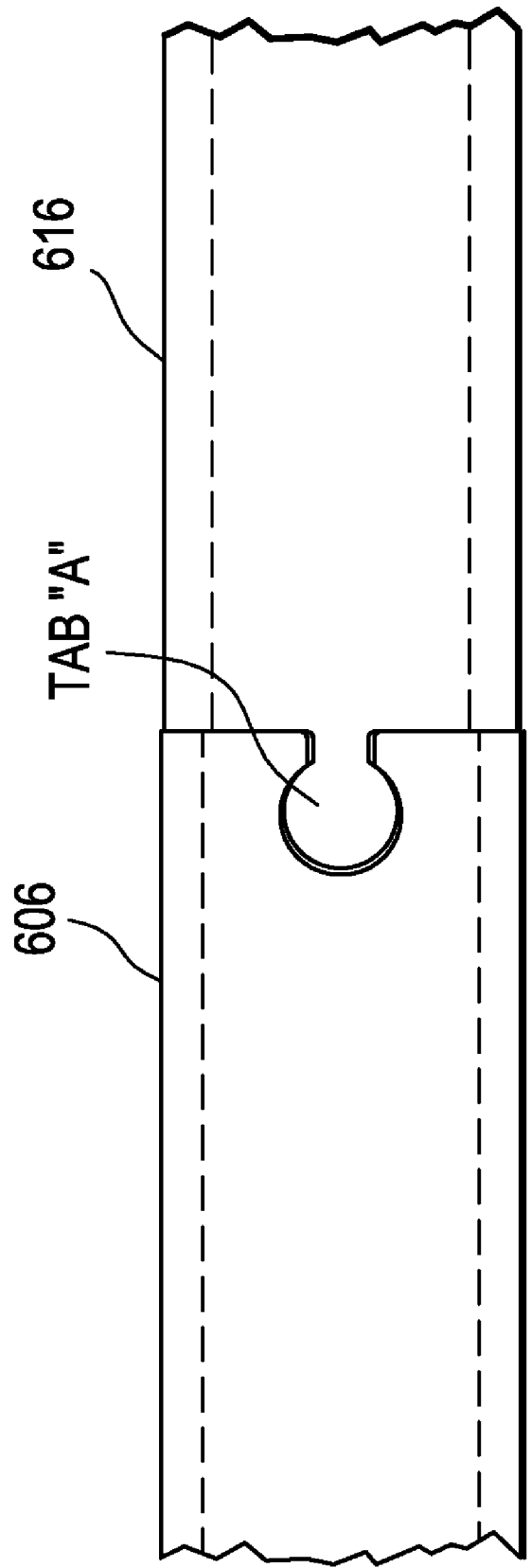

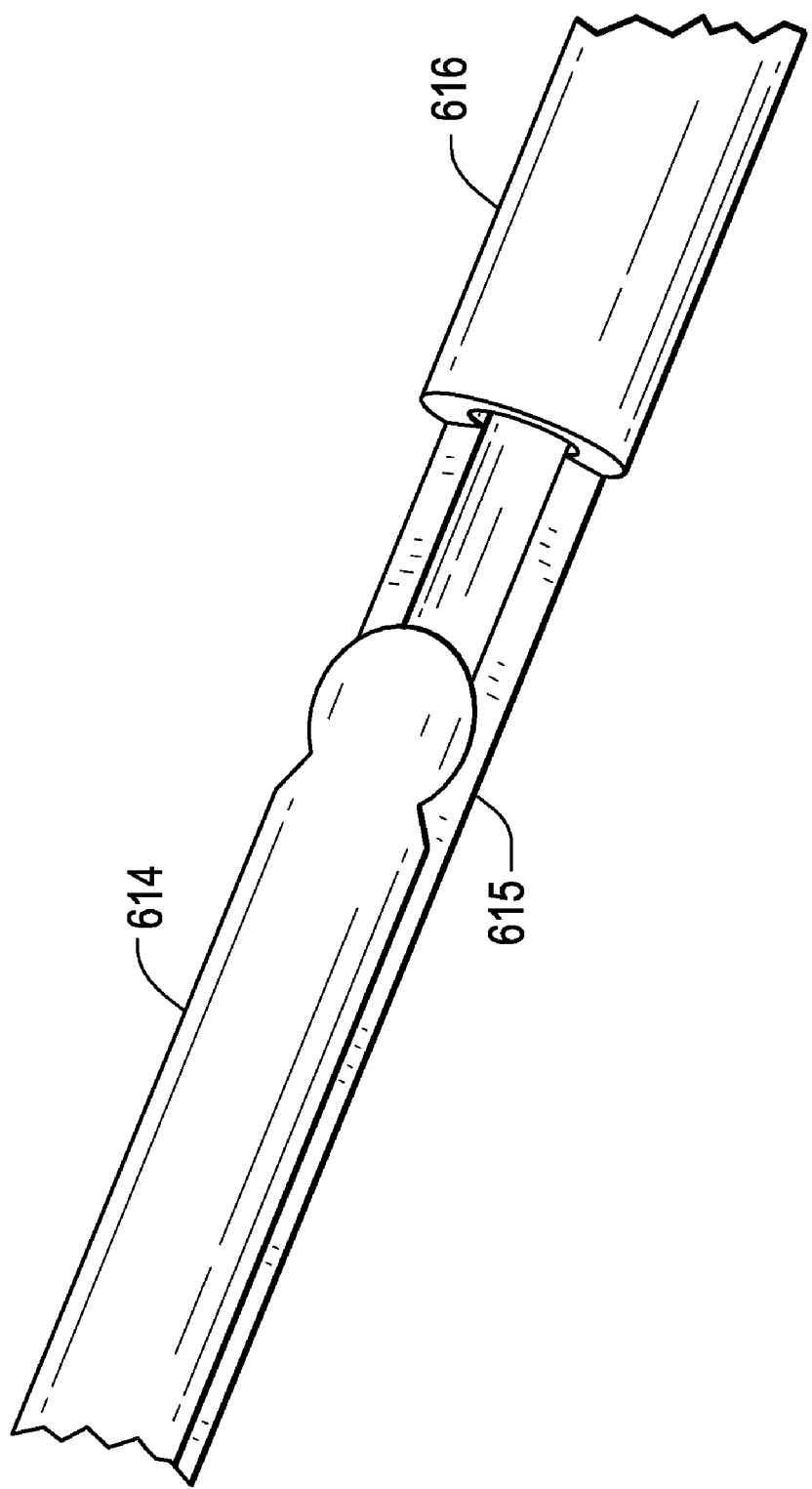

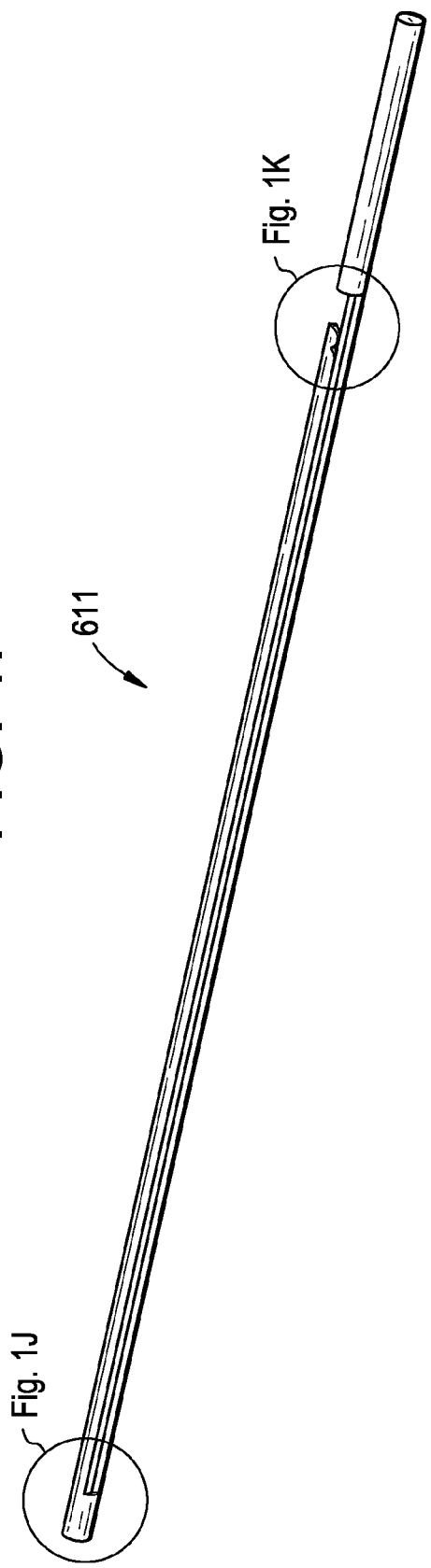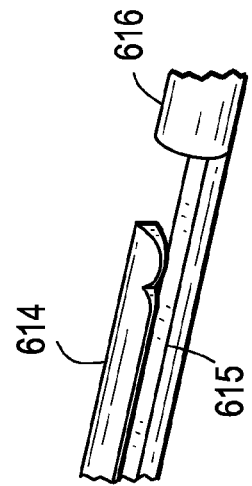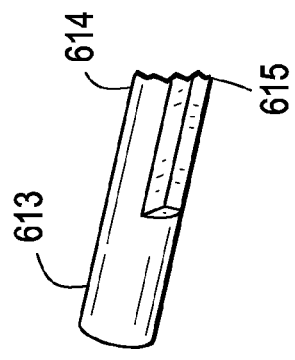

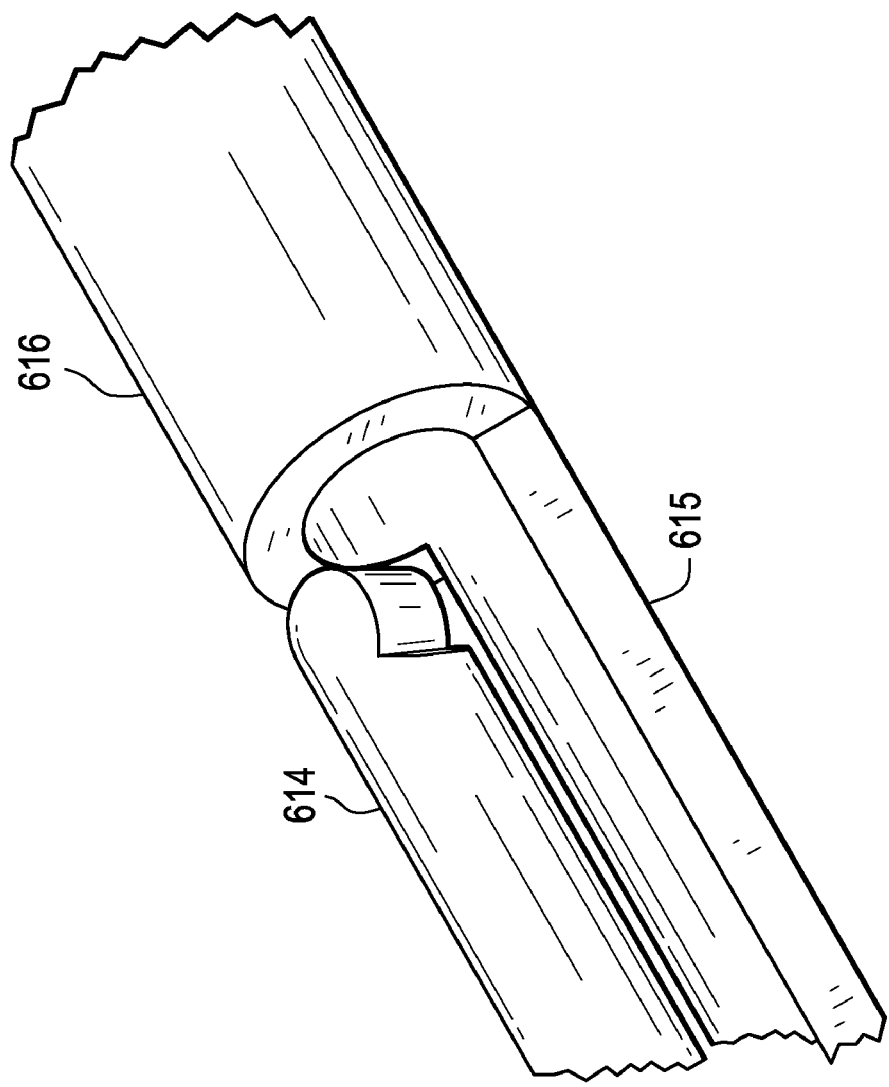

STEERABLE CATHETER SYSTEM

CROSS-REFERENCE TO RELATED APPLICATION

This application claims the benefit of U.S. Provisional Applications, Ser. No. 60/725,679, filed Oct. 12, 2005, which is incorporated by reference herein.

FIELD OF THE INVENTION

This invention relates to devices for navigating passageways in a body, and in particular, to a steerable catheter that can be used to navigate the tortuous anatomy of a body's vasculature.

BACKGROUND OF THE INVENTION

Steerable or deflectable tip catheters are useful in many applications, being a marked improvement over catheters with fixed tip curves. They are especially useful in the treatment and diagnosis of disease states through transluminal access techniques. Steerable or deflectable tip catheters are particularly useful in the fields of interventional cardiology, neurology, and endovascular diagnosis and treatment of disease where access to the disease or treatment site is accomplished through the arterial or venous vasculature.

There are presently several useful designs of steerable tip catheters. One such steerable tip catheter is described in Reissue Pat. No. 34,502. The catheter has an elongated catheter body and tip portion that can be deflected into a semi-circle in one direction. In addition, the catheter body and tip portion can be rotated. Therefore by tip deflection, catheter rotation and catheter translation, i.e., lengthwise movement of the catheter, contact of the tip portion with most areas of a heart chamber may be made.

There are, however, structures and irregularity in the heart chambers that often make access difficult. In some cases it is necessary to reach around obstacles to contact a desired site. Moreover, it may be necessary to use a longer or shorter deflectable tip portion to reach a particular site and maintain adequate stable contact.

One early multidirectional deflectable tip catheter had a catheter body and tip with 5 lumens, i.e., a central lumen and four outer lumens disposed symmetrically around the central lumen. This catheter had four puller wires that extended through the outer lumens. The distal ends of the puller wires were attached to a ring at the tip and the proximal ends were attached to a "joy stick". The central lumen was open at its distal end and connected to a luer hub at its proximal end. This catheter had no reinforcement in its body or tip. It was not suitable for electrophysiology because it had effectively no torque transmission to the tip, which made tip rotation difficult. Moreover, the catheter body was subject to the same deflection as the tip, but to a lesser degree.

A more recent steerable catheter has a steerable tip that is controlled by a bendable control handle. Multiple puller wires connect the steerable tip to this control handle, which can be bent in any direction and can be thought of as a multiple ball joint with friction. The tip, once deflected, can be further deflected laterally by an internal stylette. The disadvantage of this catheter design is that the tip is very soft and has poor lateral stiffness due to the presence of the stylette, which cannot transmit torque effectively. Because of this, an electrode at the tip of the catheter cannot be held firmly against the myocardial wall.

Another recent steerable tip catheter comprises a deflectable tip that can be deflected in one direction by a puller wire and further deflected laterally by an internal stylette. The stylette can also be moved axially within the catheter to change the shape of the tip curvature. The disadvantage of this catheter design is that the lateral stiffness of the tip is dependent upon the stylette, which cannot transmit torque effectively. In a design wherein the tip is rotated by means of a stylette, it follows that the lateral stiffness of the tip must be less than that of the stylette alone. This is because some torque from the stylette is required to rotate the tip. Moreover, the stylet must be kept small to allow the catheter body and tip to bend and to be safe within the patient body and heart.

SUMMARY OF THE INVENTION

This invention relates to a to a steerable catheter that can be used to navigate the tortuous anatomy of a body's vasculature. In one embodiment of the invention a deflectable tip catheter comprises an elongate catheter body having proximal and distal ends and defining a longitudinal axis. An inner body is coaxially disposed and slideably engaged within the elongate catheter body, the inner body having proximal and distal portions and defining a longitudinal axis. The distal portion of the inner body includes first and second strut members having proximal and distal ends and arranged in spaced apart opposition parallel to the longitudinal axis. The proximal end of the first strut member is cooperatively associated with the proximal portion of the elongate inner body. The distal end of the first strut member is cooperatively associated with the distal end of the second strut member. The proximal end of the second strut member is cooperatively associated with the distal end of the elongate catheter body. A support structure is coaxially disposed over the inner body.

In another embodiment of the invention, the deflectable catheter further includes a handle for receiving movement from a clinician, and transferring that movement into linear movement for actuation of the deflectable tip.

In another embodiment, an actuator is attached to the handle and provides the mechanism for transferring the linear movement supplied by the handle to the deflectable tip.

In still another embodiment of the invention, a catheter sheath is coaxially disposed over the elongate catheter body to protect the deflectable tip catheter.

BRIEF DESCRIPTION OF THE DRAWINGS

FIG. 1B is a side view illustrating the deflectable tip assembly according to one embodiment of the present invention.

FIG. 1C is a top view illustrating the deflectable tip assembly according to one embodiment of the present invention.

FIG. 1F is a side view illustrating the partial deflection of the tip assembly according to one embodiment of the present invention.

FIG. 1G is a magnified section view of the connection point between the actuator and the body of the inner catheter body according to one embodiment of the present invention.

FIG. 1H is a perspective view illustrating a section of the inner catheter assembly according to one embodiment of the present invention.

FIG. 1I is a perspective view illustrating the inner catheter assembly according to one embodiment of the present invention.

FIG. 1J is a perspective view illustrating a section of the distal end of the inner catheter assembly according to one embodiment of the present invention.

FIG. 1K is a perspective view illustrating a section of the inner catheter assembly according to one embodiment of the present invention.

FIG. 1M is a perspective view illustrating a section of the inner catheter assembly according to one embodiment of the present invention.

DETAILED DESCRIPTION OF THE INVENTION

The various figures show embodiments of a steerable catheter according to one embodiment of the present invention. The devices and related methods are described herein in connection with navigating though a body's venous or arterial vasculature. However, these devices are also suitable navigating through other openings or passageways in the body, including any duct within a mammalian's body, or any body vessel including but not limited to any vein, artery, duct, vessel, passageway, trachea, ureters, esophagus, as well as any artificial vessel such as grafts.

Figure 1A:
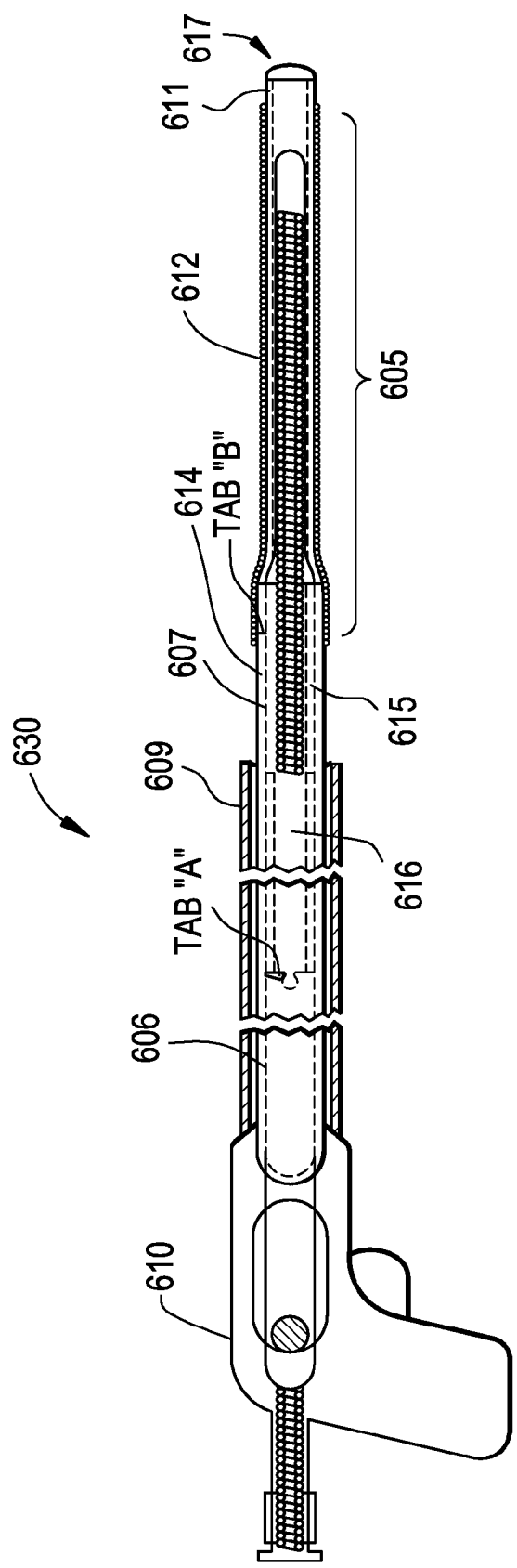
FIG. 1A illustrates a device used to navigate a body vasculature according to one embodiment of the present invention.

FIG. 1A illustrates a device used to navigate a body vasculature according to one embodiment of the present invention.

One embodiment of the steerable catheter device 630 comprises a deflectable tip assembly 605, an actuator 606, a catheter shaft 607, a catheter sheath 609 and a handle 610.

The catheter sheath 609 is the outermost elongate tube-like structure defining a longitudinal axis and sized to house the tip assembly 605, elongate catheter shaft 607, and actuator 606 during delivery. The main function of the catheter sheath 609 is to protect the steerable catheter device 630, as well as the body lumen, during delivery. The catheter sheath 609 is attached along its proximal end to handle 610.

Catheter sheaths are well known in the art. In one embodiment of the invention, the catheter sheath 609 can be made from various polymeric materials, or combination of polymeric materials known to one of skill in the art. In a preferred embodiment, the outer catheter sheath 609 is constructed from poly(ethylene)s, poly(amide)s, poly(urethane)s, poly(tetrafluroethylene)s, or a combination of these materials. Still other polymeric materials may also be used for catheter sheath 609, including, poly(carbonate)s and/or poly(imide)s. In addition, embodiments of the sheath could include reinforcement materials, e.g., metallic braid and high tensile strength polymeric braid.

Another embodiment of the steerable catheter device 630 excludes the catheter sheath 609. In this embodiment an introducer sheath, as is known in the art, may be employed to assist delivery of the steerable catheter device 630 into the vasculature.

The handle 610 is operated by a clinician to deflect the deflectable tip assembly 605 in the desired direction. As such, the handle has a means for receiving movement from the clinician, and transferring that movement into linear movement for actuation of deflectable tip assembly 605.

The deflectable tip assembly 605 further comprises an inner catheter body 611 and support structure 612 coaxially disposed over the inner catheter body 611. The support structure 612 acts to constrain the inner catheter body 611 when deflecting. The deflectable tip assembly 605 terminates with an atraumatic distal tip 617 to limit damage and trauma as the steerable catheter device 630 is used to navigate the tortuous anatomy of the body. In one embodiment, the atraumatic distal tip 617 includes a rounded open end member, as illustrated in FIG. 1A, integrated into the distal end of the inner catheter body 611.

The inner catheter body 611 is a substantially rigid structure made from a biocompatible material, such as, for example surgical stainless steel, Nitinol, or Cobalt—Chromium alloys. It should be understood that these materials are not meant to limit the scope of the invention. The support structure may come is several forms, but is preferably a coil-like structure capable of readily bending when deflected axially, yet sufficiently rigid against radial expansion. In a preferred embodiment, the coil is made from platinum—iridium, however other metallic and non-metallic materials exhibiting the necessary properties may be used.

Figure 1D:
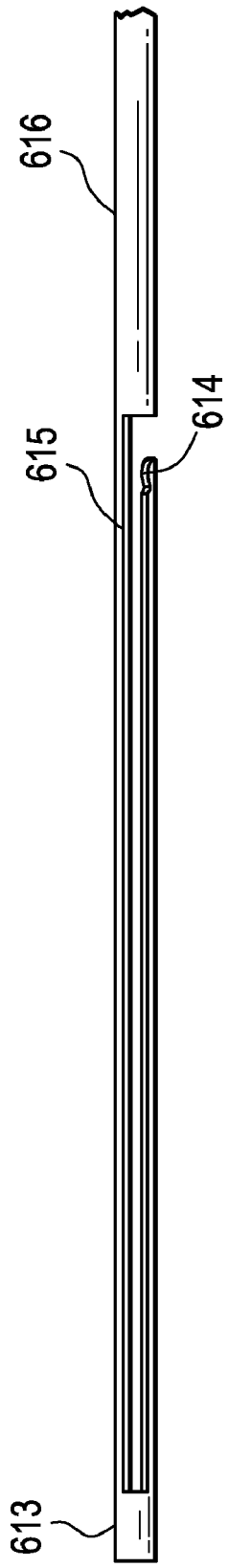
FIG. 1D is a side view illustrating the inner catheter assembly according to one embodiment of the present invention.
Figure 1E:
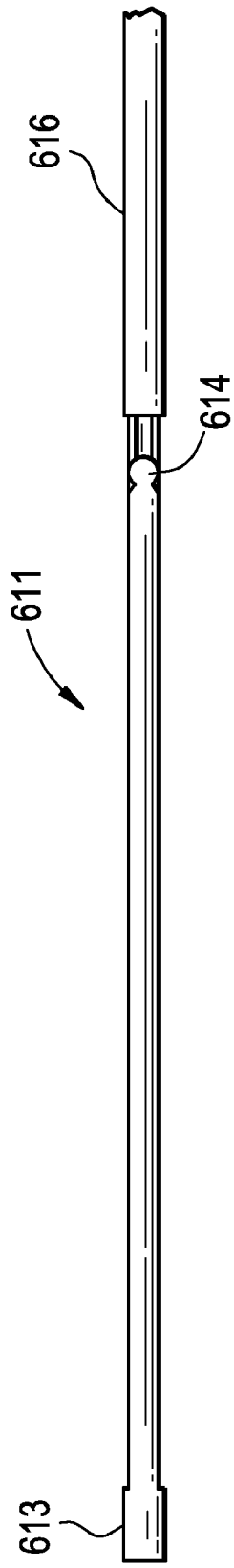
FIG. 1E is a top view illustrating the inner catheter assembly according to one embodiment of the present invention.
Figure 1L:
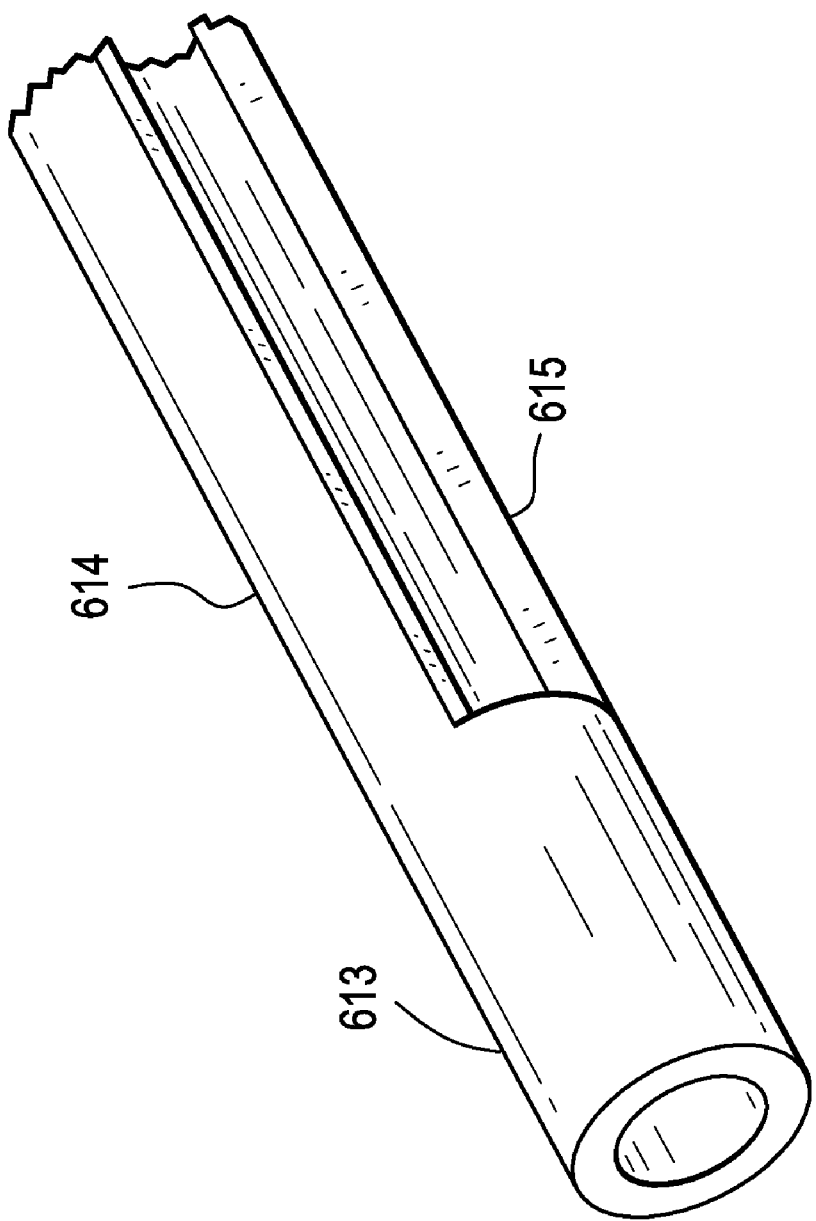
FIG. 1L is a perspective view illustrating a section of the distal end of the inner catheter assembly according to one embodiment of the present invention.

FIGS. 1B and 1C are side and top views, respectively, illustrating the deflectable tip assembly 605 defined along a longitudinal axis according to one embodiment of the present invention. To assist the deflectable tip assembly 605 in deflecting, the inner catheter body 611 is comprised of a blunt tip 613 connected along its proximal end to longitudinally arranged strut members—tang 614 and a spine 615. In a preferred embodiment, tang 614 and spine 615 are in spaced apart opposition parallel or substantially parallel to the longitudinal axis. The spine 615 is further connected to the proximal inner catheter body 616. The proximal end of the tang 614 ends with a tab (tab B). Accordingly, Tab B is located at or near the proximal end point of the arc assumed by the deflecting tip assembly 605. FIGS. 1D and 1E are side and top views, respectively, illustrating the inner catheter assembly 611 defined along the longitudinal axis according to one embodiment of the present invention.

Tab B on the tang 614 is connected to catheter shaft 607 as illustrated in FIGS. 1C and 1D. As disclosed above, the purpose of this connection point is to provide an end point for the inner catheter body 611 when deflecting in an arcuate form. However, one of skill in the art would understand that the catheter shaft 607 could be made an integral part of the deflectable tip assembly 605. FIG. 1F is a side view illustrating the partial deflection of the tip assembly 605 according to one embodiment of the present invention.

The catheter shaft 607 is a tube-like biocompatible structure substantially coaxial with catheter sheath 609, and diametrically sized such that the actuator 606 is slideably engaged with catheter shaft 607. That is to say, the outer diameter of actuator 606 is smaller than the inner bore diameter of catheter shaft 607, allowing the actuator 606 to slide within the catheter shaft 607.

In one embodiment of the invention, the catheter shaft 607 is made from a flexible material such that it can navigate the tortuous vessel anatomy when being delivered percutaneously. However, the catheter shaft 607 must also have the necessary longitudinal stiffness or "pushability" to be able to resist translational movement of the inner body 616. In a preferred embodiment, the catheter shaft 607 is made from stainless steel, a nickel titanium alloy, such as Nitinol, or Cobalt—Chromium alloy, but any material exhibiting the desired characteristics of flexibility and push-ability may be used.

The proximal end of the body 616 is attached to an actuator 606 at Tab A. The proximal end of the actuator 606 is attached to the handle 610 and provides the mechanism for transferring the linear movement supplied by the handle 610 to the deflectable tip assembly 605. This linear movement results in the inner catheter body 611 deflecting deflectable tip assembly 605 up or down, depending on the movement imparted by the handle 610. Accordingly, the actuator 606 must be rigid enough to transmit the linear movement, yet flexible enough to endure the tortuous vessel anatomy when the steerable catheter assembly is delivered through the body's vasculature. One of skill in the art would understand that the actuator 606 could be made an integral part of the deflectable tip assembly 605. FIG. 1G is a magnified section view of the connection point between the actuator 606 and the body 616 of the inner catheter body 611 according to one embodiment of the present invention.

As previously disclosed, the curved shape of the steerable catheter assembly 630 may be assumed by mechanical manipulation, such as through manipulation of the actuator 606. Referring again to FIGS. 1D and 1E, the inner catheter body 611 is shown and described as having separate components (body 616, spine 615, tang 614 and tip 613). However, it should be understood that the inner catheter body 611 is broken down into separate components for ease of illustration and explanation. In a preferred embodiment of the invention, the body 616, spine 615, tang 614 and tip 613 are formed as a monolithic unit from a single piece of material.

As previously described, the actuator 606 is slideably engaged with catheter shaft 607, and thus can freely move within catheter shaft 607. The tang 614 is attached to the catheter shaft 607 at Tab B, such that the catheter shaft 607 and tang 614 cannot move relative to one another.

In one embodiment of the invention, a complimentary receptacle is cut or formed in the distal end of the catheter shaft 607 sized to receive the Tab B and mechanically affixes Tab B to the catheter shaft 607. however, one of skill in the art would understand that Tab B might be attached to catheter shaft 607 by any suitable connection means, and this attachment mechanism should not be considered a limiting feature of the present invention. One of skill in the art would understand that other attachment means may also be employed, such as by welding, gluing, pinning, crimping, or the like.

Similarly, the proximal end of body 616 is attached to the distal end of actuator 606 at Tab A, such that the body 616 and actuator 606 cannot move relative to one another. This design allows the body 616 and the actuator 606 to be made from two separate components. However, the body 616 and the actuator may be made as monolithic units from a continuous tube, in which case there would be no attachment point between actuator 606 and body 616 at Tab A.

Spine 615 is not attached to the catheter shaft 607, and is free to move within the catheter shaft. The spine 615 of inner catheter body 611 is rigidly attached to the distal end of body 616 such that any movement of body 616 is translated directly to the spine 615. To deflect the inner catheter body 611, the actuator 606 is translated relative to the catheter shaft 607. This movement is translated to the spine 615, which is free to move relative to the catheter shaft 607. Since the tang 614 of inner catheter body 611 is fixedly attached to the catheter shaft 607, the distal end of the catheter shaft 607 will act as the proximal end point from which the arcuate form of the inner catheter body 611 deflects. This transformation from linear motion to a curved or rotational form is directly proportional to the length of the spine 615 relative to the tang 614 that is exposed from the distal end of the catheter shaft 607. Lengthening the exposed spine 615 relative to the tang 614 will deflect the distal end of the catheter assembly 630 in a first direction. Similarly, shortening the exposed length of the spine 615 relative to the tang 614 will deflect the distal end of the catheter assembly 630 in the opposite direction. When the exposed lengths of the tang 614 and the spine 615 are equal, the distal end of the catheter assembly 630 is substantially straight.

Referring to FIG. 1A, if the actuator 606 is translated distally, the spine 615 is translated distally relative to the catheter shaft 607 and deflects the inner catheter body 611 upward. Similarly, if the actuator 606 is translated proximally, the spine 615 is translated proximally relative to the catheter shaft 607, and deflects the inner catheter body 611 downward.

In a preferred embodiment, the inner catheter body 611 is fabricated to resume a pre-determined configuration when the force providing the translation of the actuator 606 is removed. One material exhibiting shape memory or super-elastic characteristics is Nitinol.

Nitinol is utilized in a wide variety of applications, including medical device applications as described above. Nitinol or NiTi alloys are widely utilized in the fabrication or construction of medical devices for a number of reasons, including its biomechanical compatibility, its biocompatibility, its fatigue resistance, its kink resistance, its uniform plastic deformation, its magnetic resonance imaging compatibility, its ability to exert constant and gentle outward pressure, its dynamic interference, its thermal deployment capability, its elastic deployment capability, its hysteresis characteristics, and is moderately radiopaque.

Nitinol, as described above, exhibits shape memory and/or super-elastic characteristics. Shape memory characteristics may be simplistically described as follows. A metallic structure, for example, a Nitinol tube that is in an Austenitic phase may be cooled to a temperature such that it is in the Martensitic phase. Once in the Martensitic phase, the Nitinol tube may be deformed into a particular configuration or shape by the application of stress. As long as the Nitinol tube is maintained in the Martensitic phase, the Nitinol tube will remain in its deformed shape. If the Nitinol tube is heated to a temperature sufficient to cause the Nitinol tube to reach the Austenitic phase, the Nitinol tube will return to its original or programmed shape. The original shape is programmed to be a particular shape by well-known techniques.

Super-elastic characteristics may be simplistically described as follows. A metallic structure for example, a Nitinol tube that is in an Austenitic phase may be deformed to a particular shape or configuration by the application of mechanical energy. The application of mechanical energy causes a stress induced Martensitic phase transformation. In other words, the mechanical energy causes the Nitinol tube to transform from the Austenitic phase to the Martensitic phase. By utilizing the appropriate measuring instruments, one can determined that the stress from the mechanical energy causes a temperature drop in the Nitinol tube. Once the mechanical energy or stress is released, the Nitinol tube undergoes another mechanical phase transformation back to the Austenitic phase and thus its original or programmed shape. As described above, the original shape is programmed by well know techniques. The Martensitic and Austenitic phases are common phases in many metals.

Medical devices constructed from Nitinol are typically utilized in both the Martensitic phase and/or the Austenitic phase. The Martensitic phase is the low temperature phase. A material is in the Martensitic phase is typically very soft and malleable. These properties make it easier to shape or configure the Nitinol into complicated or complex structures. The Austenitic phase is the high temperature phase. A material in the Austenitic phase is generally much stronger than the material in the Martensitic phase. Typically, many medical devices are cooled to the Martensitic phase for manipulation and loading into delivery systems. When the device is deployed at body temperature, they return to the Austenitic phase.

Other materials that have shape memory characteristics may also be used, for example, some polymers and metallic composition materials. It should be understood that these materials are not meant to limit the scope of the invention. Other biocompatible materials capable of exhibiting similar properties may be suitable.

Various other modifications, adaptations, and alternative designs are of course possible in light of the above teachings. Therefore, it should be understood at this time that within the scope of the appended claims the invention might be practiced otherwise than as specifically described herein.

What is claimed is:

1. A deflectable tip catheter comprising:
    an elongate catheter body having proximal and distal ends and defining a longitudinal axis;
    an inner body coaxially disposed and slideably engaged within the elongate catheter body, the inner body having proximal and distal portions and defining a longitudinal axis, the distal end portion terminating with an atraumatic distal tip, the distal portion including first and second strut members having proximal and distal ends and arranged in spaced apart opposition parallel to the longitudinal axis, wherein the proximal end of the first strut member is cooperatively associated with the proximal portion of the elongate inner body, the distal end of the first strut member is cooperatively associated with the distal end of the second strut member, and the proximal end of the second strut member is cooperatively associated with the distal end of the elongate catheter body; and
    a support structure coaxially disposed over the inner body.

2. The deflectable tip catheter of claim 1 wherein the elongate catheter comprises stainless steel.

3. The deflectable tip catheter of claim 1 wherein the elongate catheter comprises a nickel titanium alloy.

4. The deflectable tip catheter of claim 1 wherein the elongate catheter comprises a cobalt-chromium alloy.

5. The deflectable tip catheter of claim 1 wherein the inner body comprises a nickel titanium alloy.

6. The deflectable tip catheter of claim 1 wherein the proximal and distal portions of the inner body are assembled from separable component parts.

7. The deflectable tip catheter of claim 1 wherein the proximal and distal portions of the inner body are made as a monolithic unit, fabricated from a single piece of material.

8. The deflectable tip catheter of claim 1 wherein the distal portion of the inner body is made as a monolithic unit, fabricated from a single piece of material.

9. The deflectable tip catheter of claim 1 wherein the distal portion of the inner body is fabricated from separate component pieces mechanically fastened together.

10. The deflectable tip catheter of claim 1 wherein the proximal portion of the inner body is a substantially tubular structure.

11. The deflectable tip catheter of claim 1 wherein the first and second strut members have semicircular cross-sectional areas.

12. The deflectable tip catheter of claim 1 wherein the inner body further comprises a distal tip cooperatively associated with the distal ends of the first and second strut members.

13. The inner body of claim 12 wherein the distal end of the first and the second strut members are cooperatively associated with the distal tip.

14. The inner body of claim 12 wherein the distal tip is a hollow tubular structure.

15. The deflectable tip catheter of claim 1 wherein the support structure comprises a coil-like structure.

16. The deflectable tip catheter of claim 15 wherein the support structure comprises platinum-iridium.

17. The deflectable tip catheter of claim 1 wherein the support structure comprises an axially deflectable tubular structure.

18. The deflectable tip catheter of claim 1 further comprising an actuator having proximal and distal ends, the distal end of the actuator cooperatively associated with the proximal portion of the inner body.

19. The deflectable tip catheter of claim 18 wherein the actuator is a hollow tube-like structure.

20. The deflectable tip catheter of claim 18 wherein the actuator and inner body are separable.

21. The deflectable tip catheter of claim 18 wherein the actuator and inner body are made as a monolithic unit, fabricated from a single piece of material.

22. The deflectable tip catheter of claim 18 wherein the actuator and inner body are fabricated from separate component pieces mechanically fastened together.

23. The deflectable tip catheter of claim 1 further comprising a handle cooperatively associated with the proximal portion of the inner body, the handle adapted to provide linear movement of the inner body.

24. The deflectable tip catheter of claim 23 wherein the handle is attached to the proximal end of the actuator.

25. The deflectable tip catheter of claim 1 further comprising a catheter sheath coaxially disposed over the elongate catheter body.

* * * * *